(12) United States Patent
Iwasaki

(10) Patent No.: US 7,045,135 B2
(45) Date of Patent: May 16, 2006

(54) **COMPOSITION OF *KOJI* OF RICE BRAN AND NON-PROPAGATING LACTIC ACID BACTERIA, METHODS OF USE, AND MANUFACTURING METHOD THEREOF**

(75) Inventor: Teruaki Iwasaki, Sapporo (JP)

(73) Assignee: Kabushiki Kaisha Genmai Koso (JP)

( * ) Notice: Subject to any disclaimer, the term of this patent is extended or adjusted under 35 U.S.C. 154(b) by 420 days.

(21) Appl. No.: 10/368,666

(22) Filed: Feb. 19, 2003

(65) Prior Publication Data

US 2003/0157127 A1 Aug. 21, 2003

Related U.S. Application Data

(62) Division of application No. 09/951,789, filed on Sep. 13, 2001, now Pat. No. 6,843,994.

(30) Foreign Application Priority Data

Mar. 19, 2001 (JP) .................................. 2001-079104

(51) Int. Cl.
*A61K 35/78* (2006.01)

(52) U.S. Cl. .................................. 424/195.15; 424/750

(58) Field of Classification Search ................ 424/94.1, 424/195.15, 439, 750, 757, 780; 426/18, 426/31, 60; 435/254.1, 254.3
See application file for complete search history.

(56) References Cited

U.S. PATENT DOCUMENTS

| 4,358,462 | A | * | 11/1982 | Takeda | ......................... 426/13 |
| 5,498,412 | A | * | 3/1996 | Fujie | ........................... 424/729 |
| 6,395,310 | B1 | * | 5/2002 | Iwasaki | ...................... 424/725 |
| 6,623,771 | B1 | * | 9/2003 | Yamamoto | .................... 426/53 |
| 2002/0172667 | A1 | * | 11/2002 | Iwasaki | ..................... 424/94.1 |

FOREIGN PATENT DOCUMENTS

JP     2001-231551     *     8/2001

* cited by examiner

*Primary Examiner*—Ralph Gitomer
(74) *Attorney, Agent, or Firm*—McKee, Voorhees & Sease, P.L.C.

(57) ABSTRACT

In view of the finding that keeping a healthy body is fundamental for overcoming cancer, it is an object of the present invention to provide a nutritious composition that is effective in suppressing mutagenic substances and promoting good health. The composition also suppresses large intestinal cancer. The composition includes dietary fiber in a range of 15 wt % to 30 wt % in respect to the total amount of composition which is contained in dried koji fine powder that includes dead fungi of *Aspergillus* and active enzyme produced by the *Aspergillus*.

9 Claims, No Drawings

COMPOSITION OF *KOJI* OF RICE BRAN AND NON-PROPAGATING LACTIC ACID BACTERIA, METHODS OF USE, AND MANUFACTURING METHOD THEREOF

CROSS-REFERENCE TO RELATED APPLICATION

This application is a division of application Ser. No. 09/951,789 filed Sep. 13, 2001 now U.S. Pat. No. 6,843,994, which claims priority to Japanese Application 2001-79104 filed Mar. 19, 2001.

FIELD OF THE INVENTION

This invention relates to a nutritious supplemental composition for preventing the onset of large intestinal cancer.

In particular, in the present invention, rice bran is heated with steam and *Aspergillus*, which may be *Aspergillus oryzae* strain, for example. The ingredients are mixed, cultivated and ripened to make rice bran koji. The *Aspergillus* is then annihilated, and the enzyme groups produced by *Aspergillus* are changed into dried koji fine powder under conditions that preserve the catalytic activity of the enzyme.

Either dietary fiber aiming at removal of mutagen or plant protein acting as nutritious element is contained in the composition. The present invention relates to the nutritious supplemental composition for suppression against onset of large intestinal cancer and its manufacturing method.

DESCRIPTION OF THE RELATED ART

Cancer is generally defined as a malignant tumor. Causes for oncogenesis are roughly classified into chemical oncogenesis with carcinogenic substance and viral oncogenesis.

A number of carcinogen substances are classified as chemical oncogenesis substances. With respect to viral oncogenesis, it is apparent that the number of types exceed 100 types or more. In addition, it has become apparent that a reason why cancer occurs is due to a combination of chemical oncogenesis substances and a specific person's genes. More than 100 type of oncogenes have been reported.

In recent years, aberrant crypt foci (ACF) have been shown to appear as precancerous lesions of the large intestine in a rat following an initial dosing of carcinogenic substances (azoxymethane=AOM, for example). This lesion has also been found to be present in humans. These ACF are therefore assumed to be one of the important indexes for prevention of onset of large intestinal cancer.

A mutagen is something that changes the character of a cell. There are "direct mutagens", such as nitroso compound or antiseptic agent, for example, that directly derange the genes in a cell, and "indirect mutagens" that are activated in a human body by an enzyme, such as the decomposition product of amino acid or protein found in scorched meat or fish or like, for example. It is believed that aberrant crypt foci generated by the "mutagen" are precancerous lesins of the large intestine have a high possibility of becoming large intestinal cancer in the future.

Experiments have shown that substances that suppress against "aberrant crypt foci" can suppress approximately 70% of large intestinal cancer which is onset by the "aberrant crypt foci". Further, in contrast to carcinostatic chemotherapy, it has recently been thought that a direct breakage of cancer cell under application of biophylaxis of the host through killer cells or immunocomplement cells or enforcement of biological function that indirectly retracts cancer by reinforcing the function of the organism by applying biological response modifier (BRM) has been advocated in the medical field.

Along with this trend, a study about medicines or foods for activating an immune system has also been promoted and has frequently shown that the foods derived from bacteria or mycete, for example, lactobacillus lactis, lactic acid coccus, cultivated basidiomycetes mycelioid (*Aspergillus*), fruit body of mushroom or the like stimulate activation against the surface of leukocyte membrane. For instance, both production and discharging of cytokine (a general term for non-antibody protein such as lymphokines that assist in cellular immunity by stimulating either monocyte or macrophage or the like with groups of soluble substances discharged by sensitized limphocyte contacted with specific antigens, which in turn may act as an intercellular regulation factor when an immune response occurs) are applied through stimulation of the immune system with a component (generally called an LPS) constituted by cell walls of beta-glucan contained in plant or gram-negative bacteria such as lactic acid bacteria or the like.

In addition, it is often said that some foods derived from plants or animals, for example, chlorella, *Nemacystus decipiens* and other sea weeds (sulfuric acid polysaccharide), green and yellow leaf vegetables (carotenoid and others), fruits or the like (polyphenols and the like), beans (soybean peptide), rice bran (arabinoxylan and others), nucleic acid (salmon DNA), crusts (chitin, chitosan), shells (zinc, selenium) and the like show a mechanism for adjusting metabolic activity in leukocyte cells, for example, activation of metabolism enzyme by sulfide contained in vegetables. In turn, it has been made apparent academically that vegetables (spinach, field pea, burdock, yam, nettle tree mushroom, mushroom, ginkgo nut, corn, green peas, or the like) or fruits (orange, grape fruit, mandarin range, apple or the like) have superior actions and effects against suppression against production of mutagen in a human body, inactivation of mutagen, suppression against metabolism activation of mutagen, inactivation against mutagen or metabolism activation and suppression against fixation of mutation of gene or the like. That is, a cancerous cell shows a cytodieresis by transmitting a specific signal within the cell itself even if a certain signal regarding proliferation is not received due to an irregularity in its receptor related to proliferation. In this case, it is known that pigment systems such as carotenoid or the like contained in vegetable juice and the like may improve the irregular state of the cell receptor. Effective constituents acting as anti-mutagen substances contained in these vegetables and the like are, for example, vitamins e.g. vitamin C, proline (a type of α-amino acid), thio proline, glutathione (having a reducing action), cysteine (α-amino acid containing sulfur atom, wherein —SH in its structure is important for bioactivity), compound of sulfur and hydrogen, and dietary fiber and the like.

Reduction in carbohydrate metabolism causing derangement of metabolism function regarding nourishment has been shown as an index for aging. The peak age for carbohydrate metabolism function of a human is about 65-year age, which becomes progressively deranged. Hypergasia in nutritious metabolism including carbohydrate metabolism may product a lack in energy at each of the secretion organs, which may generate a series of other syndromes.

A tremendous number of Japanese people suffering from gastric cancer in recent years were found overwhelmingly to be associated with an increase in ingestion of meat and a decrease in the number of vegetables. This has resulted in an increased rate of onset of large intestinal cancer and a large number of mammary cancers. The rate of onset of mammary cancers in Japan has also increased. If it is assumed that a rate of death classified by statistical age for cancers in recent Japan is defined as a numerical value of 1 for age 24 or 25, the rate of death over age 40 is nine times higher. This value increases exponentially by age, i.e. by 29 times for people in their fifties, by 70 times for persons in their sixties and by 152 times for persons in their seventies. It is possible to say that this numerical value is proportional to a trend of reduction in immunity function accompanied by a reduction in metabolism function caused by the aforesaid aging.

It is believed that the increased meat causes either *Clostridium perfringens* or *Escherichia coli* colibacillus to become predominant within intestine and further promote proliferation of toxic bacteria, resulting in blood derangement produced by derangement of tissue or gangrene from gas derived from toxic bacteria, and large intestinal cancer becomes onset. In addition, scorching of protein as found in meat or hamburger under application of heat causes carcinogen substances such as Trp-p-1, Trp-p-2 or the like to be generated, wherein the carcinogen substances may promote not only large intestinal cancer but also mammary cancer and prostatic cancer. However, the ability to ingest a large amount of vegetables or dietary fibers is seriously questionable in view of meal configurations and digestive capability.

SUMMARY OF THE INVENTION

The present inventor has performed a wider and deeper study to develop a nutritious supplemental food that everybody can take in an easy manner, showing a high food value and superior absorbability. In view of studies showing that suppression of aging of a human body is attained by intake of balanced nutrition and activation of metabolism through improved environment of tissue cell in organism, keeping a healthy condition itself results in activation of immune function to prevent and suppress various kinds of sicknesses. As a result, dietary fiber is included in a cereal constituent containing undevitalized enzyme with rice bran koji as a major constituent. This constituent provides well-balanced nutrition, and contributes to improvement of cell environment to promote activation of metabolic and immune function. Additionally, this constituent may prevent active oxygen in a human body from becoming mutagenic and further suppress onset of aberrant crypt foci.

Further, the present inventor believes that 6-phytase produced by *Aspergillus* in the constituent of the present invention decomposes phytin in a plant (calcium salt and magnesium salt of myoinosithexaphosphate), and facilitates its absorption, so that it is not necessary to ingest large amounts of vegetables or dietary fiber.

In the present invention, the following technical means have been set in order to resolve the aforesaid problems.

The rice bran is steamed, *Aspergillus* strain colony is cultivated and ripened to attain rice bran koji, and *Aspergillus* is diminished to attain dried substances including dead fungi, enzyme groups produced by the *Aspergillus* strain colony that are contained in the dried koji fine powder under a state in which catalysis of the enzyme itself is not lost. This constituent includes either dietary fiber or plant protein. In this case, cereal or the like such as unpolished rice is cultivated by *Aspergillus* together with rice bran and lactic acid bacteria.

A practical configuration of the present invention is as follows.

(1) A nutritious supplemental composition for suppression against onset of large intestinal cancer, wherein the capability of catalysis of enzyme groups produced by *Aspergillus* is maintained and dietary fiber in a range of 15 wt % to 30 wt % in respect to a total amount of composition is contained in dried koji fine powder including dead fungi of *Aspergillus*.

(2) A nutritious supplemental composition for suppression against onset of large intestinal cancer, wherein a capability of catalysis of enzyme groups produced by *Aspergillus* is maintained and plant protein in a range of 15 wt % to 30 wt % in respect to a total amount of composition is contained in dried koji fine powder including dead fungi of *Aspergillus*.

(3) A nutritious supplemental composition for suppression against onset of large intestinal cancer, wherein a capability of catalysis of enzyme groups produced by *Aspergillus* is maintained, dietary fiber in a range of 15 wt % to 30 wt % in respect to a total amount of composition and plant protein in a range of 15 wt % to 30 wt % in respect to a total amount of composition are contained in dried koji fine powder including dead fungi of *Aspergillus*.

(4) A nutritious supplemental composition for suppression against onset of large intestinal cancer according to any one of (1) to (3), wherein dead fungi of lactic acid bacteria are also included in said dried koji fine powder.

(5) A nutritious supplemental composition for suppression against onset of large intestinal cancer according to any one of (1) to (4), wherein said dried koji is rice bran koji.

(6) A nutritious supplemental composition for suppression against onset of large intestinal cancer according to (5), wherein either a single or mixed crop koji selected from rice bran koji, barley koji, corn koji, bean koji, and barley bran koji are contained in said rice bran koji in a range of 5 wt % to 30 wt %.

(7) A method for manufacturing a nutritious supplemental composition for suppression against onset of large intestinal cancer, wherein after *Aspergillus* is cultivated and ripened at steamed rice bran, a temperature of ripened product is kept at 44° C. to 46° C., the ripened product (koji) is formed into dried rice bran koji containing dead fungi of *Aspergillus* while keeping a capability of catalysis of enzyme groups produced by *Aspergillus* and further changed into fine powder and dietary fiber powder is uniformly mixed with the dried rice bran koji fine powder under a state in which there is no difference in their humidity.

(8) A method for manufacturing a nutritious supplemental composition for suppression against onset of large intestinal cancer, wherein after *Aspergillus* is cultivated and ripened at steamed rice bran, a temperature of ripened product is kept at 44° C. to 46° C., the ripened product (koji) is formed into dried rice bran koji fine powder containing dead fungi of *Aspergillus* while keeping a capability of catalysis of enzyme groups produced by *Aspergillus* and further formed into fine powder, and the plant protein powder is uniformly mixed with said dried rice bran koji powder under a state in which there is no difference in their humidity.

(9) A method for manufacturing a nutritious supplemental composition for suppression against onset of large intestinal cancer according to any one of (7), (8), wherein after *Aspergillus* and lactic acid bacteria are cultivated and ripened, the ripened product is formed into dried rice bran koji containing dead fungi of *Aspergillus* and lactic acid bacteria while maintaining a capability of catalysis of enzyme groups produced by *Aspergillus*.

Unpolished rice surface contains the rind, seed coat and powder layers which occupy about 5% of the entire unpolished rice, while the embryo bud occupies about 3% of entire unpolished rice. These portions are peeled off by rice cleaning operation and are defined as rice bran. In addition to glycoprotein, minerals or vitamins, the embryo bud and seed coat of rice bran contain phytin acid (myoinositheraphosphate, its abbreviated symbol $IP_6$) in the form of phytin (calcium salt, magnesium salt of phytin acid), myoinositol (known as a part in which phosphorus acid is removed from phytic acid, a part of vitamin B complex required for growth of yeast or growth of mouse, and as carcinostatic substance), arabinoxylan, ferulic acid (having functions to diminish radical of anticoagulate, diminish active oxygen and prevent onset of large intestinal cancer), amino butyric acid ($\alpha$-amino acid of which small amount is present in protein, this is related to respiration of brain tissue), polysaccharide, antioxidant, and unsaturated fatty acid or the like.

Almost all natural proteins contained in the embryo bud are glycoprotein coupled to sugar. Although the physiological function of the sugar chain of glycoprotein is not yet well understood, the functions of the sugar chain are already known to be deeply related to cognizance of inter-cells by difference in shape of sugar chains, and migration in organism and protein metabolism of the cell or the like. It is believed that inflammation caused by mutagenetic substances, such as active oxygen or bacteria and the like, may induce variation in sugar chain binding as well as cognizance disability of the inter-cell, resulting in that either immunodeficiency or decompensation is produced.

Lactic acid bacteria decompose sugar substances contained in rice bran. It has been reported that lactic acid bacteria die in heat of 41° C. or higher, and that dead fungi have some effects against constituents in the cell that activate various kinds of immunologic reactions in the organism, thereby providing high antitumor action or infection protection. It has also been reported that a single dose of lactic acid bacteria in addition to dietary fiber has a scavenging effect (cleaning action) in which the number of cancer cells showing liver metastasis is restricted.

The constituent in the present invention comprises dried powder such as plant leaves, stalks, seeds (beans, seeds) having a high amount of dietary fibers. Protein is a major constituent of dietary fibers. Cellulose is a major constituent of the cell wall of a plant (polysaccharide that is a basic substance of plant fiber occupying about 1/3 of the plant), hemicellulose (polysaccharide of plant cell wall closely related to xylan, manna, galactans and others), lignin (aromatic polymer substance present in ligneous cell wall), pectin (gelatin-like acid polysaccharide present as inter-cell substance of plant), alginic acid (polysaccharide of phlegm forming a cell membrane of sea weeds) and glucomannan (polysaccharide having, as its major constituent, mannose) or the like. It is apparent that polysaccharide (macromolecular sugar chain) activates leukocyte, stimulates a cytokine network, activates hormone systems, and further activates immune function. These dietary fibers are classified as water-soluble dietary fiber and insoluble dietary fiber. The water-soluble dietary fiber reduces blood serum cholesterol and suppresses an increase in blood sugar value during postprandial state. Insoluble dietary fiber adsorbs either carcinogen substances or carcinogen promoting substances in the intestine and discharges them out of the human body. It has also been reported that pectin of water-soluble dietary fiber suppresses large intestinal cancer. In addition, large amounts of phytin acid and myoinositol contained in a plant as a form of phytin are known as carcinostatic substances.

It has been found by an animal model induced with large intestinal cancer that all phytic acid, myoinositol and inositol compounds are superior in preventing the onset of abberant crypt foci. An experiment with a nude mouse dosed with these combined substances reported suppression of the onset of large intestinal cancer, fibrosarcoma and mammary cancer, or the like. In humans, dosing of 1 to 2 g per day of phytic acid and myoinositol shows an effect of preventing large intestinal cancer. For a person having a high risk of onset of large intestinal cancer, a dose of twice this amount is sufficient.

An academic report has shown that phytic acid is not only a carcinostatic substance, but is also effective in preventing arteriolosclerosis, senescence, and anti-oxidation action. In accordance with this academic report, an organism has an enzyme known as glutathione-S-transferase (GST) that detoxicates chemical substances, i.e. mutagen coming from an external environment into a human body and inactivates it. When an experimental rat is dosed with phytic acid (2% of feed), the GST activation characteristic for inactivating chemicals containing these carcinogen substances in the liver increases, causing a significant decrease in mutagenic substances.

There is an academic report stating that phytic acid itself not only prevents large intestinal cancer, but also effectively suppresses against large intestinal cancer in combination with green tea (concentration of 2%). Further, the large intestinal cancer suppressive effect can be improved in with myoinositol having phosphoric acid removed from phytic acid. As for a rat, this phytic acid is decomposed by 6-phytase derived from small intestine mucosa (enzyme processed with hydrolysis to remove 6-phosphoric acid) and absorbed. As for a human, activation of 6-phytase derived from small intestine mucosa is quite low as compared with that of rat, so that it can be scarcely absorbed unless 6-phytase derived from food is also present. In addition, phytic acid is hardly absorbed when combined with protein. In view of this, protein decomposing enzyme in accordance with the present invention decomposes protein, and 6-phytase produced by *Aspergillus* performs a hydrolysis reaction against phytin and phytic acid to absorb phytic acid ($IP_6$), although it is decomposed into $IP_5$, $IP_4$, $IP_3$ and myoinositol and the like, and may be easily absorbed. In addition, either magnesium or calcium or the like is separated from the phosphoric acid group and becomes easily absorbed. In view of this, even if a large amount of dietary fibers containing phytin are not taken, it is possible to attain a substantial effect of phytic acid as well as a substantial effect of myoinositol. Phytic acid reaches various organs in about one hour after administration and has an immediate effect.

The constituent of the present invention containing large amounts of these substances described above is well balanced in its nutrition and contains high amounts of biophylaxis activating substances. When a person takes about 20 g of this constituent every day as nutritious supplemental food in a continuous manner, his or her regular food together with this supplemental food synergistically improves cell environment of cells. As a result, the cell gets energy, and a metabolic and immune function and the like are improved, thereby improving health. In addition, substances for suppressing "mutagen" that are abundantly contained in this composition may eliminate "mutagen", restrict onset of precancerous lesions of large intestinal cancer, resulting in a superior effect in suppressing large intestinal cancer. In particular, when 6-phytase generated by *Aspergillus* is taken, it performs a hydrolysis reaction for phytic acid in a form of phytin to cause it to be well absorbed, so that it is possible to attain an efficient pharmacodynamic action of myoinositol as well as phytic acid contained in the composition of the present invention, even if a large amount of vegetables or dietary fibers are not taken.

As herein defined, a "product temperature" means a temperature of raw material wherein heat is generated at a culture bed through *Aspergillus* cultivation. As "rice bran koji", it also contains koji in which crop koji is mixed at a rate of 30% or less.

The present invention has the following superior effects.

(1) If a large amount of the composition of the present invention described in claim 1 are taken into a body, each of the enzymes of which large amounts are contained may perform a catalysis action within the body. Protein is decomposed into low molecular moles to enable amino acid to be supplied, then protein may organically compose amino acid for the organism's cells. In addition, one part of the dietary fiber is decomposed with enzyme, and the other part of the dietary fiber is non-soluble, goes to the colon, adsorbs carcinogen, discharges it out of the body, and stimulates the intestine wall to eliminate constipation. The dead fungi are decomposed with enzyme in the body, and absorbed into the body so as to activate immunologic reactions.

6-phytase generated by *Aspergillus* in the composition of the present invention performs a hydrolysis action against phytic acid in a form of phytin to cause it to be easily absorbed. Accordingly, even if a large amount of vegetables or dietary fiber is not taken, either phytic acid or myoinositol can be efficiently absorbed, the composition may reach various organs in about one hour after administration, and may attain an accumulative effect capable of realizing its action immediately.

Vitamins, minerals and other nutritious elements abundantly contained in the composition of the present invention become energy of cells in the organism and improve the environment of the cells, and improve metabolic function as well as immune function. These accumulative effects may prevent aging to keep the body healthy, while at the same time suppressing onset of large intestinal cancer.

(2) The composition of the present invention described in claim 2 contains plant protein in dried koji powder keeping a capability of catalysis of enzyme proper, so that in addition to the effects described in the above item (1), it has some effects that even if a person does not supply protein additionally, mere taking of the present composition enables the person to take sufficient plant protein, the protein is supplied to the cell as amino acid and acts against sugar chain of the cell and the composition of amino acid in an organic manner. As described above, the present invention is capable of contributing to recover and maintain a healthy condition, and suppress onset of large intestinal cancer through its accumulative action.

(3) The composition of the present invention described in claim 3 containing dietary fibers and plant protein, so that it has a combined effect with those described in the above items (1) and (2).

(4) The composition described in claim 4 having less sugar due to lactic acid bacteria and dead fungi of lactic acid bacteria and demonstrating immune system stimulation with cell wall of lactic acid bacteria, production of cytokine and its discharge.

(5) The invention described in claim 5 whereby nutrition at the embryo bud of unpolished rice can be utilized concentrically.

(6) The composition described in claim 6 containing either a single or mixed crop koji selected from rice koji, barley koji, corn koji, bean koji, and barley bran koji, so that they may supplement food and provide an effect that is preferably cumulative.

(7) The manufacturing method described in claim 7 to manufacture uniform rice bran koji. In addition, dried rice bran koji fine powder can be provided so that the groups of enzyme produced by *Aspergillus* may not lose the ability to catalyze enzymes. The dietary fiber is mixed with the rice bran koji fine powder under uniform conditions of temperature and humidity so as to provide a uniform density, resulting in a composition effective in preventing large intestinal cancer that can be easily manufactured.

(8) The manufacturing method described in claim 8 for manufacturing uniform rice bran koji. In addition, dried rice bran koji fine powder can be provided in such a way that the groups of enzyme produced by *Aspergillus* may not lose the capability of catalyzing enzyme proper. The plant protein fine powder is mixed with the rice bran koji fine powder under uniform temperature and humidity conditions to provide a uniform density, resulting in a composition that is effective in preventing onset of large intestinal cancer that can be easily manufactured.

(9) The manufacturing method described in claim 9 whereby the dried rice bran koji contains less sugar by decomposing the sugar produced by lactic acid bacteria.

DESCRIPTION OF THE PREFERRED EMBODIMENTS

Preferred embodiments of the present invention will be described as follows.

Method Preferred Embodiment 1

Selected rice bran is put into a water applying machine, water in an amount of about 25 wt % to 30 wt % in regard to raw material is added, and water is sufficiently absorbed into the selected rice bran to cause the bran to bulge. The bulged bran is put into a steamer, calcareous powder (baked oyster shell powder=grain size #250 mesh to #400 mesh) is added by about 0.5 wt % to 1 wt %, respectively, and these materials are steamed with steam of 100° C. to 120° C. for about 50 to 60 minutes while their moisture is checked. When crops such as unpolished rice are applied, they are steamed together with rice bran.

Rice bran that is completely steamed is released to cool down to about 37° C. to 40° C. and *Aspergillus* strain colony, *Aspergillus oryzae* strain, for example, is added by about 0.1 wt % and are well mixed.

In this case, it is possible to use *Aspergillus* selected from other kojis (A. Kawachii, A. Awamori, A. Usami). In addition, as needed, a small amount of lactic acid bacteria (of about $2.5 \times 10$ pieces/g to $3.0 \times 10^2$ pieces/g) is added. If required, the same amounts of yeast and lactic acid bacteria as those of *Aspergillus* can be added.

*Aspergillus* strain colony vigorously secretes decomposing enzymes such as amylase, protease and lipase or the like to decompose sugar and protein contained in rice bran into low molecules. The lactic acid bacteria decomposes sugar. Temperatures suitable for cultivation of *Aspergillus* and lactic acid bacteria is 35° C. to 37° C. and humidity of 85% RH to 90% RH, and activity in bacteria is stopped under a humidity of 70% RH or less. Raw material having *Aspergillus* and lactic acid bacteria is cultivated for 32 to 36 hours while temperature and humidity are adjusted in a stepwise manner in a range of room temperature of 35° C. to 37° C. and in a range of humidity of 50% RH and 90% RH.

The rice bran at the culture bed are not closely contacted with each other by calcareous powder uniformly adhered to the surfaces of the rice bran to form a proper degree of aeration clearance and *Aspergillus* strain colony is cultivated under a state where air flow is well kept in an average manner.

At the culture bed, its temperature is increased automatically from a temperature of 25° C. to 38° C. gradually under application of cultivation heat of the *Aspergillus* strain colony. This state is kept for a minimum time of 8 hours. When the temperature of product (a temperature of raw material in the cultivation bed) becomes 40° C. to 41° C., the culture bed is agitated to cause the temperature of product to be forcedly decreased in such a way that an activity of species bacteria is not made dull. At this time, the temperature of product is decreased to about 32° C. and increased again up to a certain temperature.

A growing period in which ripening of *Aspergillus* strain colony is promoted is controlled at a room temperature of 31° C. to 36° C. in such a way that the temperature of the product does not exceed 40° C., and when the temperature of the product becomes 40° C. to 42° C. after 6 hours, the culture bed is agitated to decrease the temperature of the product. After this operation, both temperature and humidity are adjusted in such a way that the temperature of the product may become a range of 39° C. to 40° C. and then the material is cultured for 11 hours to 12 hours. Since the *Aspergillus* strain colony is aerobic, the agitation of culture bed is carried out for three to four times for every specified time (8 hours) during this period to supply oxygen, a color check and an odor check are performed, and further a ripening and a degree of dry are adjusted through agitation of the culture bed.

At a period of standstill in which growing of the *Aspergillus* strain colony is stopped, the humidity is adjusted to 70% RH or less where activity of *Aspergillus* is made dull and the room temperature is increased up to 36° C. to 37° C. The temperature of the product is adjusted to a range of 39.5° C. to 40° C., the product is ripened for 6 hours to attain rice bran koji. At this time, a value of pH at the culture bed is kept at 6 to 7.

After this operation, the rice bran koji at the culture bed is dried for 9 hours at a room temperature of 46° C. to 53° C. The temperature of the product is restricted to a range of 44° C. to 46° C., activities of *Aspergillus* and lactic acid bacteria are completely stopped and die out. Upon completion of the drying operation, the product becomes a dried material with a component moisture being less than 4%, 2.5% to 3.6%, respectively. In this connection, the component moisture of normal rice bran is 13 to 14%.

This dried rice bran koji is applied to a screen to remove block rigid product with a size of 5 mm or more, applied to a pulverizer to attain dried koji fine powder while a degree of fine powder is checked.

As applied to unpolished rice, three kinds of rice of different producing districts were mixed. As calcareous powder, baked oyster shell powder was selected. However, bone powder, calcium lactate, crab shells or the like can be applied and so the type of raw material is not limited.

In the case of the aforesaid method, lactic acid bacteria added in addition to *Aspergillus* is anaerobic, so that sugar is decomposed and decreased in the layer where less amount of air flow is produced at the raw material in the culture bed. This lactic acid bacteria also dies out with heat at the time of drying stage.

Method Preferred Embodiment 2

Either single crop or mixed crops selected from unpolished rice, barley, corn, soybean and barley bran are mixed with the rice bran in a range of 5 to 30 wt %, steamed and then cultivation with *Aspergillus* and lactic acid bacteria is carried out in the same manner as that of the preferred embodiment 1. A drying step after ripening is also the same as that of the preferred embodiment 1. These crops can be cultivated with *Aspergillus* separate from rice bran and mixed with it.

Then, non-heated dried dietary fiber fine powder (moisture content of 2.5% to 3.6%) of 2 wt % to 30 wt % of a total amount of composition is added to and mixed with the dried koji fine powder manufactured in this way so that there occurs no difference in humidity between the dried koji fine powder and the non-heated dried dietary fiber fine powder. That is, they are fine powder, so that if there is a substantial difference in humidity between these materials, a certain block may easily be formed when they are mixed thereby inhibiting uniformity of mixing.

As the dietary fiber is added to the dried koji fine powder, it is possible to cite, as an example for it, fine powder of all dried mushrooms (shiitake, maitake, eringi, gano-derma lucidum and others), thumbmurray (*G. pentaphyllum*), kidney bean, field pea, ashida, mugwort, spinach, *Brassica Rapa* var. *pervidis*, tea leaf, burdock, bamboo shoot, carrot, onion, green pepper, konjak, sweet potato, ginger, seed of vegetable (soy bean), rice bran, wheat bran powder, soy shell powder, sea weeds, fruits, persimmon leaf, bamboo leaf and other materials. Since these materials are powder of whole dried substances, other several nutritious constituents in addition to fibers are abundantly contained.

The dietary fibers of these vegetables and fruits show an important relation for recovering metabolic disease, adsorbing mutagenesis substances in the large intestine and eliminating them, so that their physiologic functions have been noticed. In addition, the dietary fibers stimulate the wall of intestine to promote hyperperistalsis and eliminate constipation.

As a drying step for vegetables and fruits, it is preferable to apply a non-heated frozen low temperature drying. The dietary fiber fine powder having dried vegetables can be mixed in a range of 2 wt % to 30 wt % in respect to the total amount of constituent. Further, the dietary fibers extracted from these vegetables can be applied.

| Blending Preferred Embodiment 1 | |
|---|---|
| Dried rice bran koji fine powder | 75 wt % |
| Dried rice koji fine powder | 10 wt % |
| Soybean fine powder | 10 wt % |
| Thumbmurray fine powder | 3 wt % |
| Mugwort fine powder | 2 wt % |
| Blending Preferred Embodiment 2 | |
| Dried rice bran koji fine powder | 80 wt % |
| Dried crop koji fine powder | 10 wt % |
| Ashitaba leaf fine powder | 4 wt % |
| Spirulina fine powder | 4 wt % |
| Tea leaf fine powder | 2 wt % |
| Blending Preferred Embodiment 3 | |
| Dried rice brari koji fine powder | 70 wt % |
| Dried rice koji fine powder | 10 wt % |
| Mushroom (Ganoderma) fine powder | 5 wt % |
| Ashitaba leaf fine powder | 7 wt % |
| Tea leaf fine powder | 2 wt % |
| Ginger powder | 1 wt % |
| Soy bean protein | 5 wt % |

-continued

Blending Preferred Embodiment 4

| | |
|---|---|
| Dried rice bran koji fine powder | 80 wt % |
| Ashitaba leaf fine powder | 2 wt % |
| Kidney bean fine powder | 2 wt % |
| Seaweed fine powder | 1 wt % |
| Soy bean protein | 15 wt % |

Blending Preferred Embodiment 5

| | |
|---|---|
| Dried rice bran koji fine powder | 80 wt % |
| Dried rice koji fine powder | 10 wt % |
| Seaweed (*Hizikia fusiforme*) fine powder | 3 wt % |
| Spirulina | 5 wt % |

Mushrooms (Maitake, gano-derma lucidum, Agarisk, shiitake [*Lentinus edodes*] and others) contain large amounts of constituents suppressing mutagenesis substances, such as fibrous constituents, phytic acid in a form of phytin, β-glucan or the like. In particular, it has already been made clear that β-glucan breaks tumor cell by activating immunocomplement cells in the organism, resulting in retrocession of cancer. It has also been reported that an experiment on prostatic cancer cell of a human body demonstrated that β-D-glucan induces a self-destruction inducing action.

Gingers contain protein decomposing enzyme and have an anti-bacterial action.

Seaweeds contain large amounts of fibrous substances and also large amounts of iodine promoting activation of hypophysis cerebri hormone. A requirement of iodine per day for an adult person is set to 300 to 400 μg.

In addition, it is also possible to mix non-heated plant protein of 5 wt % to 30 wt % in respect to the total amount of composition with dried koji fine powder.

As the plant protein, it is possible to use soybean powder, soybean protein, *Spirulina* and corn powder or the like. These substances supply non-heated protein and decompose enzyme in a human body to absorb amino acid.

*Spirulina* described above is a blue-green algae well grown in salt water, contains fibrous substance and chlorophyll and 60% of its entire volume is protein having stable amino acid.

Blending Preferred Embodiment 1

| | |
|---|---|
| Dried rice bran koji fine powder | 70 wt % |
| Dried rice koji fine powder | 10 wt % |
| Soybean protein | 20 wt % |

Blending Preferred Embodiment 2

| | |
|---|---|
| Dried rice bran koji fine powder | 65 wt % to 80 wt % |
| Soybean protein | 20 wt % to 35 wt % |

Blending Preferred Embodiment 3

| | |
|---|---|
| Dried rice bran koji fine powder | 70 wt % |
| Spirulina powder | 5 wt % |
| Soybean protein | 25 wt % |

Blending Preferred Embodiment 4

| | |
|---|---|
| Dried rice bran koji fine powder | 85 wt % |
| Dried crop koji fine powder | 10 wt % |
| Spirulina powder | 5 wt % |

It is possible that dietary fiber fine powder with a range of 2 wt % to 30 wt % in respect to a total amount of composition and plant protein fine powder with a range of 5 to 30 wt % in respect to a total amount of composition are mixed with dried koji fine powder.

Blending Preferred Embodiment 1

| | |
|---|---|
| Dried rice bran koji fine powder | 70 wt % |
| Dried rice koji fine powder | 10 wt % |
| Soybean protein | 15 wt % |
| Seaweeds fine powder | 2 wt % |
| Ashitaba fine powder | 3 wt % |

Blending Preferred Embodiment 2

| | |
|---|---|
| Dried rice bran koji fine powder | 65 wt % |
| Dried rice koji fine powder | 10 wt % |
| Soy bean protein | 20 wt % |
| Konjak powder | 1 wt % |
| Barley bran fine powder | 1 wt % |
| Shiitake [*Lentinus edodes*] fine powder | 3 wt % |

Blending Preferred Embodiment 3

| | |
|---|---|
| Dried rice bran koji fine powder | 70 wt % |
| Dried rice koji fine powder | 5 wt % |
| Soy bean protein | 10 wt % |
| Barley bran fine powder | 1 wt % |
| Konjak fine powder | 3 wt % |
| Ashitaba fine powder | 3 wt % |
| Shiitake [*Lentinus edodes*] fine powder | 5 wt % |
| Seaweeds fine powder | 2 wt % |
| Tea leaf fine powder | 1 wt % |

Excipient material to be described later is added to single dried koji fine powder and mixed fine powder. Particles are then formed with a grain size of 1.2 mm to 1.3 mm using a granulating machine, which are then packaged into a bag with weight of 3.5 g, 5 g and the like by a packaging machine after drying operation. In the alternative, the particles are not formed into granules, but instead are formed into tablets by a tablet forming machine.

The raw materials are not limited to the aforesaid excipient materials, but may include others later described. Further, the raw materials may be mixed using a wide range of methods, and may be blended to make particles or form tablets.

| | |
|---|---|
| Glucose | 4 wt % to 12 wt % |
| Lactose | 12 wt % to 20 wt % |
| Plant oil and fat | 2 wt % to 6 wt % |

Accumulative analysis of major compositions per 100 g of composition (rice bran koji by 65%, rice koji by 10%, soy bean protein by 20% and shiitake [*Lentinus edodes*] powder by 5%) manufactured in this way is as follows.

| | |
|---|---|
| Number of lactic acid bacteria | 243,000 pieces/g to 253,000 pieces/g |
| Titer of amilase | 3200 U/g to 3400 U/g |
| Titer of neutric protease | 366 U/g to 383 U/g |
| Titer of lipase | 524 U/g to 536 U/g |
| Saccharide | 18.2 g to 18.5 g |
| Protein (including amino acid) | 22.4 g to 24.8 g |
| Dietary fiber | 18.5 g to 19.3 g |
| Phytic acid | 3.86 to 4.23 g |
| Moisture | 2.6 g to 3.4 g |
| Energy | 426 to 445 Kcal |

Since the dried vegetables contain at least 70% fiber, it is possible to increase the amount of dietary fiber in the composition by 20% to 40% in reference to a blending amount. With this increased amount of fiber, the amount of phytic acid can also be increased.

It is possible to increase the amount of protein included in the composition of the present invention in proportion to the amount of plant protein. Each of the aforesaid blending amounts is not limited to the indicated values.

The present inventor performed a short term experiment with rats to determine prevention of oncogenesis and suppression of its onset with anti-mutagenesis substances using precancerous lesions of the large intestine as an index. In the instant example, the present inventor performed a study regarding prevention of oncogenesis of large intestinal cancer using the composition of the present invention with target azoxymethane=AOM acting as carcinogens with an aberrant crypt foci induced at a rat large intestine being used as an index. The composition of the present invention included rice bran koji 65%, rice koji 10%, soy bean protein 20% and gano-derna lucidum fine powder 5 wt %.

(1) Method of Experiment

Male rats F344 5-weeks of age in five groups were used. 15 mg/kg azoxymethane was dosed subcutaneously in each of 12 rats of one group to four groups for one week and for two weeks after starting the experiment. For the second to fourth groups, the composition of the present invention was mixed with a fundamental meal at a concentration of each of 1.25%, 2.5% and 5% and dosed in feed for each of experimental periods (five weeks). As for the fifth group (four rats), no azoxymethane was administered, but only the composition of the present invention was mixed by 5% and fed to the rats. Upon completion of the experiment, the rats were killed and their colons were fixed in formalin, thereafter they were dyed with methylene blue and a quantitative observation of aberrant crypt foci was carried out.

(2) Result of Experiment

In each of the groups, no significance difference was found in their average weight. Aberrant crypt foci of colon were found only in the first to fourth groups. Each of average aberrant crypt foci for large intestines in the first to fourth groups was

| First group: | 139.5 ± 27.7 |
| Second group: | 122.6 ± 27.7 |
| Third group: | 99.0 ± 24.1 |
| Fourth group: | 79.0 ± 18.4 |

Each of the number of aberrant crypt foci of the third and fourth groups was significantly low (P<0.01) compared with the first group.

The foci were classified in reference to the number of foci constituting the aberrant crypt foci. The value was low for one foci (P<0.05 or P<0.01) in any of the second to fourth groups as compared with the first group, the value was low for two foci (P<0.05 or P<0.01) in any of the third and fourth groups as compared with the first group, and the value was low (P<0.05) in more than four foci as compared with that of first group.

(3) Consideration

Study of this experiment has made it clear that dosing of the composition of the present invention may suppress onset of aberrant crypt foci induced at a rat colon. It is estimated that this effect of suppression of onset of aberrant crypt foci causes the composition of the present invention to prevent large intestinal cancer of a human body.

Next, the present inventor performed a long term experiment for the prevention of oncogenesis by administrating the composition of the present invention in the model of oncognesis of rat large intestinal cancer induced by carcinogens, i.e. azoxymethane=AOM.

(1) Method of Experiment

Male rats F344 of five-week age were classified into 7 groups with one group being constituted by 30 rats, sixth group and seventh were excluded, and azoxymethane=AOM of 15 mg/kg was dosed subcutaneously by a total of three times once/week from the first week to the third week after starting the experiment.

The first group was fed basic food for an experimental period. Each of the second group and the third group was fed with mixed substances of 5% and 2.5% of the composition of the present invention, respectively, for five weeks after starting the experiment, and subsequently, they were fed basic food. The fourth group and the fifth group were fed basic food up to the fifth week, and each of 5% and 2.5% of the composition of the present invention was mixed with the basic food and fed. The sixth group and the seventh group were not fed azoxymethane=AOM and only 5% of the composition of the present invention and the basic food were fed to the rats during the period of experiment.

After feeding for 40 weeks, all the rats were killed and a rate of onset and the number of onset of the tumor at the colon were compared.

(2) Result of Experiment

At the time of killing the rats, the average weight in each of the groups showed a slight decreasing trend in the group administered azoxymethane as compared with that of nonprocessed group (the seventh group). Further, in the groups (the fourth, fifth and sixth groups) where the composition of the present invention had been dosed for a long period of time, a significant difference was not found in the weight ratio of liver and kidney of each of the groups.

Examination with the naked eye showed that large intestinal tumors were found only in the first to fifth groups.

The incidence of tumors in the first to fifth groups was:

| First group: | 51.9% (14/27) |
| Second group: | 55.6% (15/27) |
| Third group: | 47.8% (11/23) |
| Fourth group: | 18.5% (5/27) |
| Fifth group: | 34.6% (9/26) |

It was confirmed that a trend of suppression against onset of tumor in the fourth and fifth groups occurred in response to concentration as compared with that of the first group, and the fourth group showed a decrease with a significant difference (P<0.05).

The number of onset of average tumor (multiplicity) per one rat in each of the groups was;

| First group: | 0.77 ± 0.89 |
| Second group: | 0.70 ± 0.91 |
| Third group: | 0.68 ± 0.83 |
| Fourth group: | 0.18 ± 0.39 |
| Fifth group: | 0.42 ± 0.58 |

The fourth group showed a significant decrease as compared with that of the first group (P<0.01).

(3) Consideration

In the case of model of oncogenesis of large intestinal cancer in a rat induced by azoxymethane, the composition of the present invention did not show the effect of suppression in the groups (the second and third groups) fed with the composition at an initiation phase, although in the groups (the fourth and fifth groups) where the composition of the present invention was fed at a promotion phase, it showed an effect of suppression in response to concentration and further an apparent suppression effect was found in the group (the fourth group) fed with 5% of the composition of the present invention.

As described above, the composition of the present invention is assumed to be promising in suppressing onset of large intestinal cancer in a human body. An amount of composition of the present invention which is efficient after a person takes it is about 14 g to 28 g per day and as a nutritious supplemental food taken for health reasons, about 14 g of the composition is satisfactory. As a standard value, 21 g per day is preferable.

An amount of inclusion of phytic acid in the test substance described above is 0.84 g to 0.93 g/21 g. Accordingly, increasing the amount of addition of dietary fiber enables an amount of inclusion of phytic acid also to be increased.

To the contrary, as a result of performing the experiment for 29 weeks by dosing bran containing large amounts of phytic acid and a single phytic acid of the same amount as that contained in the bran in the model of onset of oncogenesis of large intestinal cancer induced by azoxymethane under the same condition, the group dosed with phytic acid was shown to have a significant difference (a cancer onset frequency of 52.6%), although the group dosed with bran was not shown to have a significant difference (a cancer onset frequency of 70%).

In view of this fact described above, it was shown that even if a large amount of plant containing a large amount of phytic acid was taken, an effect of suppression against onset of large intestinal cancer corresponding to an amount could not be expected.

Herb medicine does not provide an immediate effect, but improves disease while recovering the person's health. The composition of the present invention also contains high amounts of nutritious elements as well as high amounts of carcinostatic substances. In particular, the fact that it contains decomposing enzyme for phytic acid provides a superior effect in suppressing the onset of large intestinal cancer, resulting in that it may provide nutrition for improving the environment of tissue cell and energy as well as improving metabolic function and immune function. It therefore has an effect similar to herb medicine as well.

Further, the present invention is not limited to the aforesaid example of form, but both selection of raw materials such as dietary fiber and plant protein or the like and their blending rate can be optionally set on a case-by-case basis.

Although the present invention has been described with reference to the preferred embodiments, it is apparent that the present invention is not limited to the aforesaid preferred embodiments, but various modifications can be attained without departing from its scope.

What is claimed is:

1. A method for manufacturing a nutritious supplemental composition for suppression against onset of large intestinal cancer comprising: cultivating *Aspergillus* with steamed rice bran at a temperature of about 40° C. or less for a time period sufficient to form ripened koji; treating the ripened koji at a temperature of 44° C. to 46° C. to stop propagation of the *Aspergillus* and form dried rice bran koji; said dried rice bran koji containing at least one enzyme produced by the *Aspergillus*, whereby the enzyme has catalytic activity; and uniformly mixing the dried rice bran koji with dietary fiber such that and there is no substantial difference in humidity between the dried rice bran koji and the dietary fiber.

2. A method for manufacturing a nutritious supplemental composition for suppression against onset of large intestinal cancer comprising: cultivating *Aspergillus* with steamed rice bran at a temperature of about 40° C. or less for a time period sufficient to form ripened koji; treating the ripened koji at a temperature of 44° C. to 46° to stop propagation of the *Aspergillus* and form dried rice bran koji; said dried rice bran koji containing at least one enzyme produced by the *Aspergillus*, whereby the enzyme has catalytic activity; and uniformly mixing the dried rice bran koji with plant protein such that there is no substantial difference in humidity between the dried rice bran koji and the plant protein.

3. A method for manufacturing a nutritious supplemental composition for suppression against onset of large intestinal cancer according to any one of claims 1 and 2 and further providing that the *Aspergillus* is cultivated with lactic acid bacteria, and further providing that the ripened koji is treated at a temperature of 44° C. to 46° C. to stop propagation of the lactic acid bacteria.

4. The method of claim 1 whereby the *Aspergillus* is cultivated with the steamed rice bran at a temperature of between 39° C. to 40° C.

5. The method of claim 1 whereby the *Aspergillus* is cultivated for a time period of about six hours.

6. A method for manufacturing a nutritious supplemental composition for suppression against onset of large intestinal cancer comprising: cultivating *Aspergillus* with steamed rice bran, at a temperature of about 40° C. or less for a time period sufficient to form ripened koji; and treating the ripened koji at a temperature of 44° C. to 46° C. to stop propagation of the *Aspergillus* and form dried rice bran koji; said dried rice bran koji containing at least one enzyme produced by the *Aspergillus*, whereby the enzyme has catalytic activity.

7. The method of claim 6 further including the step of uniformly mixing the dried rice bran koji with a substance selected from the group consisting of dietary fiber, plant protein, and combinations of the same such that there is no substantial difference in humidity between the dried rice bran koji and the dietary fiber.

8. The method of claim 7 whereby the dried rice bran koji is mixed with the substance such that the substance constitutes about 15 wt % to 30 wt % of the composition.

9. A method for manufacturing a nutritious supplemental composition for suppression against onset of large intestinal cancer comprising: cultivating *Aspergillus* and lactic acid bacteria with steamed rice bran, at a temperature of about 40° C. or less for a time period sufficient to form ripened koji; and treating the ripened koji at a temperature of 44° C. to 46° C. to stop propagation of the *Aspergillus* and the lactic acid bacteria and form dried rice bran koji; said dried rice bran koji containing at least one enzyme produced by the *Aspergillus*, whereby the enzyme has catalytic activity.

* * * * *